(12) United States Patent
Amos et al.

(10) Patent No.: US 11,523,922 B2
(45) Date of Patent: Dec. 13, 2022

(54) STENT DELIVERY SYSTEM HAVING RETENTION STRUCTURE

(71) Applicant: Boston Scientific Scimed, Inc., Maple Grove, MN (US)

(72) Inventors: Michael D. Amos, Boston, MA (US); John Lane, Manchester, NH (US); Jacob A. Graham, Watertown, MA (US); Gary J. Leanna, Holden, MA (US); Andrew K. Hollett, Waltham, MA (US); Michal Weisman, Fair Lawn, NJ (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 474 days.

(21) Appl. No.: 16/797,101

(22) Filed: Feb. 21, 2020

(65) Prior Publication Data
US 2020/0188149 A1   Jun. 18, 2020

Related U.S. Application Data

(63) Continuation of application No. 14/623,264, filed on Feb. 16, 2015, now Pat. No. 10,610,388, which is a continuation of application No. 13/164,900, filed on Jun. 21, 2011, now Pat. No. 8,979,824.

(60) Provisional application No. 61/356,872, filed on Jun. 21, 2010.

(51) Int. Cl.
*A61F 2/95* (2013.01)
*A61M 25/00* (2006.01)
*A61M 25/04* (2006.01)
*A61M 25/01* (2006.01)
(Continued)

(52) U.S. Cl.
CPC ............... *A61F 2/95* (2013.01); *A61F 2/82* (2013.01); *A61M 25/0068* (2013.01); *A61M 25/0074* (2013.01); *A61M 25/01* (2013.01); *A61M 25/04* (2013.01); *A61F 2/9522* (2020.05); *A61F 2002/9505* (2013.01);
(Continued)

(58) Field of Classification Search
CPC ...... A61M 2025/0096; A61M 25/0068; A61M 25/0074; A61M 25/01; A61M 25/04; A61M 27/002; A61F 2/82; A61F 2/95; A61F 2/9522; A61F 2002/9505; A61F 2220/0033; A61F 2002/9522; A61F 2002/95; A61F 2002/9511; A61F 2002/9528; A61F 2002/9534; A61F 2002/962; A61F 2002/966; A61F 2002/9665
See application file for complete search history.

(56) References Cited

U.S. PATENT DOCUMENTS

| | | |
|---|---|---|
| 4,382,445 A | 5/1983 | Sommers |
| 4,592,341 A | 6/1986 | Omagari et al. |
| 4,699,611 A | 10/1987 | Bowden |

(Continued)

FOREIGN PATENT DOCUMENTS

EP     1872749 A1     1/2008

*Primary Examiner* — Kai H Weng
(74) *Attorney, Agent, or Firm* — Seager, Tufte & Wickhem, LLP

(57) ABSTRACT

A stent delivery system including an elongate shaft of a medical device, a stent selectively coupled to a distal portion of the elongate shaft, and a coupling mechanism for selectively coupling the stent to the elongate shaft by inserting a tab on one of the stent or the elongate shaft into an opening in the other of the stent or the elongate shaft. The tab may be deflected from a first position to a second position to disengage the tab from the opening.

17 Claims, 22 Drawing Sheets

(51) Int. Cl.
 *A61F 2/82* (2013.01)
 *A61M 27/00* (2006.01)
(52) U.S. Cl.
 CPC .... *A61F 2220/0033* (2013.01); *A61M 27/002* (2013.01); *A61M 2025/0096* (2013.01)

(56) References Cited

U.S. PATENT DOCUMENTS

| | | |
|---|---|---|
| 4,931,037 A | 6/1990 | Wetterman |
| 4,950,228 A | 8/1990 | Knapp, Jr. et al. |
| 4,955,858 A | 9/1990 | Drews |
| 4,957,479 A | 9/1990 | Roemer |
| 4,973,301 A | 11/1990 | Nissenkorn |
| 4,990,133 A | 2/1991 | Solazzo |
| 5,052,998 A | 10/1991 | Zimmon |
| 5,152,749 A | 10/1992 | Giesy et al. |
| 5,160,341 A | 11/1992 | Brenneman et al. |
| 5,334,185 A | 8/1994 | Giesy et al. |
| 5,372,600 A | 12/1994 | Beyar et al. |
| 5,401,257 A | 3/1995 | Chevalier, Jr. et al. |
| 5,507,464 A | 4/1996 | Hamerski et al. |
| 5,599,291 A | 2/1997 | Balbierz et al. |
| 5,681,274 A | 10/1997 | Perkins et al. |
| 5,690,643 A | 11/1997 | Wijay |
| 5,824,041 A | 10/1998 | Lenker et al. |
| 5,871,537 A | 2/1999 | Holman et al. |
| 5,921,952 A | 7/1999 | Desmond, III et al. |
| 5,921,971 A | 7/1999 | Agro |
| 6,245,076 B1 | 6/2001 | Yan |
| 6,248,100 B1 | 6/2001 | De Toledo et al. |
| 6,264,624 B1 | 7/2001 | Desmond et al. |
| 6,364,887 B1 | 4/2002 | Dworschak et al. |
| 6,368,344 B1 | 4/2002 | Fitz |
| 6,562,024 B2 | 5/2003 | Alvarez De Toledo et al. |
| 6,589,251 B2 | 7/2003 | Yee et al. |
| 6,620,191 B1 | 9/2003 | Svensson |
| 7,198,637 B2 | 4/2007 | Deshmukh et al. |
| 7,763,008 B2 | 7/2010 | Yu |
| 7,879,080 B2 | 2/2011 | Sato |
| 8,133,265 B2 | 3/2012 | Seemann et al. |
| 8,211,087 B2 | 7/2012 | Carter et al. |
| 8,808,348 B2 | 8/2014 | Hollett et al. |
| 9,649,213 B2 | 5/2017 | Hollett et al. |
| 2002/0016597 A1 | 2/2002 | Dwyer et al. |
| 2003/0047654 A1 | 3/2003 | Johansson et al. |
| 2003/0114910 A1 | 6/2003 | Juhani et al. |
| 2005/0085891 A1 | 4/2005 | Goto et al. |
| 2005/0085892 A1 | 4/2005 | Goto et al. |
| 2005/0090887 A1 | 4/2005 | Pryor |
| 2005/0165352 A1 | 7/2005 | Henry et al. |
| 2006/0068144 A1 | 3/2006 | Mizuno et al. |
| 2006/0155359 A1 | 7/2006 | Watson |
| 2006/0276873 A1 | 12/2006 | Sato |
| 2007/0005122 A1 | 1/2007 | Inoue |
| 2007/0293929 A1 | 12/2007 | Aoba et al. |
| 2008/0004685 A1 | 1/2008 | Seemann et al. |
| 2009/0143849 A1 | 6/2009 | Ozawa et al. |
| 2009/0312829 A1 | 12/2009 | Aoba et al. |
| 2010/0137966 A1 | 6/2010 | Magnuson |
| 2011/0160739 A1 | 6/2011 | Amos |
| 2012/0095567 A1 | 4/2012 | Weisman et al. |

STENT DELIVERY SYSTEM HAVING RETENTION STRUCTURE

CROSS REFERENCE TO RELATED APPLICATIONS

This application is a continuation of U.S. application Ser. No. 14/623,264, filed Feb. 16, 2015, which is a continuation of U.S. application Ser. No. 13/164,900, filed Jun. 21, 2011, now granted as U.S. Pat. No. 8,979,824, which claims the benefit of U.S. Provisional Application No. 61/356,872, filed Jun. 21, 2010, the entire disclosures of which are incorporated herein by reference.

TECHNICAL FIELD

The disclosure is directed to a retention structure of a medical device. More particularly, the disclosure is directed to a stent retention structure for selectively securing a stent to a shaft of a stent delivery system. Specifically, the disclosure is directed to a retention structure for selectively securing a drainage stent to a catheter shaft

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a retention system to releasably secure a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a retention structure for selectively coupling a stent to a delivery system.

Accordingly, one illustrative embodiment is a stent delivery system including an elongate shaft of a medical device, a stent selectively coupled to a distal portion of the elongate shaft, and a coupling mechanism for selectively coupling the stent to the elongate shaft by positioning a tab on one of the stent or the elongate shaft into engagement with the other of the stent or the elongate shaft, such as inserting a tab on one of the stent or the elongate shaft into an opening in the other of the stent or the elongate shaft.

Another illustrative embodiment is a drainage stent delivery system including a drainage stent including a tubular member, an elongate shaft extending distally from a handle assembly to a location proximate the drainage stent, and an elongate member extending axially through the elongate shaft. A distal portion of the elongate shaft includes a tab configured for selective engagement with the drainage stent which extend into the lumen of the drainage stent. The elongate member is axially movable from a first position to a second position. In the second position the tab is deflected into engagement with the drainage stent by contact with the elongate member and in the first position the tab is disengaged from the drainage stent to allow the drainage stent to be released from the elongate shaft.

Another illustrative embodiment is a drainage stent delivery system including an elongate shaft of a medical device, a drainage stent including a barb configured to retain the drainage stent at an anatomical location, and a coupling mechanism for selectively coupling the stent to the elongate shaft. The coupling mechanism includes an engagement member for engaging with the barb of the drainage stent and a pull wire extending proximally from the engagement member which is actuatable to effect disengagement of the engagement member from the barb of the drainage stent.

Yet another illustrative embodiment is a method of selectively decoupling a stent from an elongate shaft of a medical device. The stent is coupled to a distal portion of an elongate shaft of a medical device with a coupling mechanism. The coupling mechanism includes a tab on one of the stent or the elongate shaft inserted into an opening in the other of the stent or the elongate shaft. The tab is moved from a second position in which the tab is engaged with the opening to a first position in which the tab is disengaged from the opening. The elongate shaft is then withdrawn proximally from the stent while the tab is in the second position.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
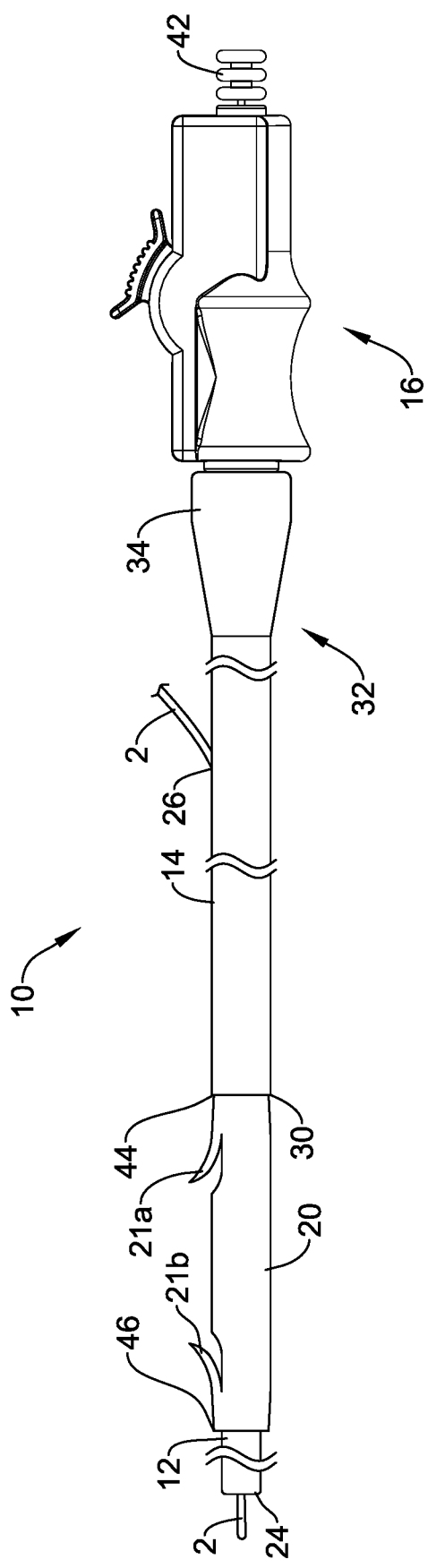
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
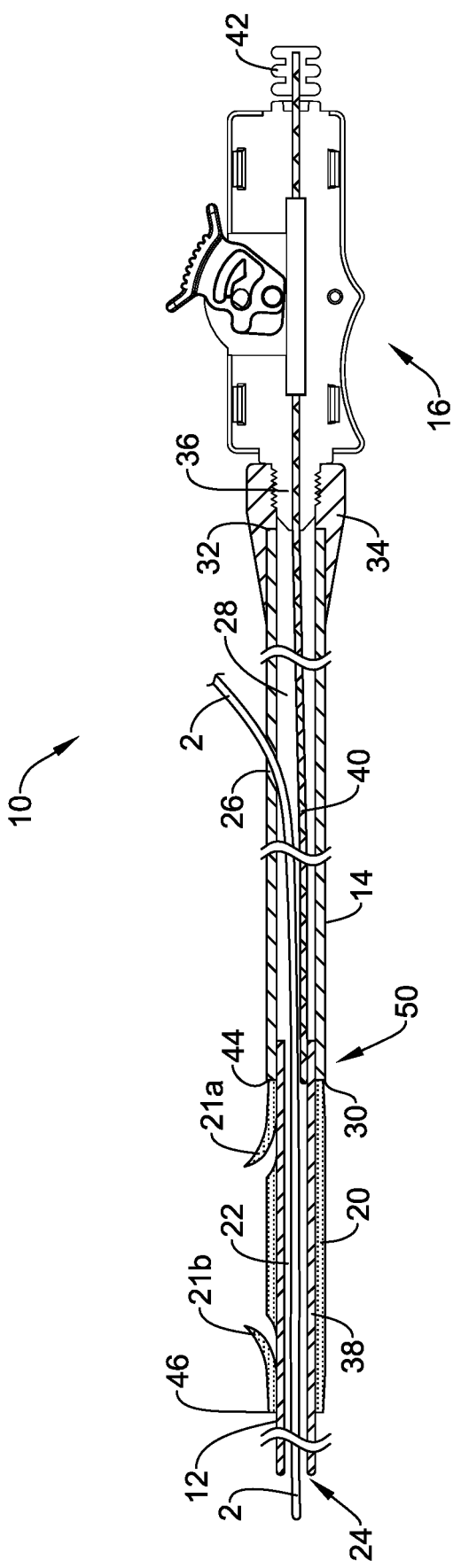
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. The drainage stent 20 may be an elongate tubular member which is generally not expandable. The drainage stent 20 may have a proximal end 44, a distal end 46 and a lumen 48 extending through the drainage stent 20 from the proximal end 44 to the distal end 46. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage stent delivery system 10 with single-operator-exchange (SOE) capabilities.

The guide catheter 12 may be slidably disposed in the lumen 28 of the push catheter 14 and extend distally from the distal end 30 of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end of the drainage stent 20 may abut and/or face a distal end or rim 30 of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The drainage stent delivery system 10 may include a means for releasably connecting the drainage stent 20 to an elongate shaft of the drainage stent delivery system 10, such as the guide catheter 12 or the push catheter 14 of the drainage stent delivery system 10. When the drainage stent 20 has been properly placed, the drainage stent 20 may be disconnected from the drainage stent delivery system 10 such that the drainage stent 20 remains in the lumen when the guide catheter 12 and/or the push catheter 14 are withdrawn. Some exemplary retention mechanisms for selectively coupling the drainage stent 20 to an elongate shaft of the drainage stent delivery system 10 are further described herein. The retention mechanisms may be used to selectively deploy, reposition and/or retrieve the drainage stent 20 during a medical procedure.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location. The elongate wire 40 may extend through the lumen 28 of the push catheter 14 to the handle assembly 16 while the distal tubular portion 38 extends through the drainage stent 20 to a location distal of the drainage stent 20. In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments axial movement of an elongate shaft of the drainage stent delivery system 10 (e.g., the guide catheter 12 and/or the push catheter 14) relative to the drainage stent 20 may disengage or unlock the drainage stent 20 from the drainage stent delivery system 10. Once the drainage stent 20 is disengaged from the guide catheter 12 and/or the push catheter 14, withdrawing the guide catheter 12 and/or the push catheter 14 proximally may release the drainage stent 20 from the drainage stent delivery system 10 in order to deploy the drainage stent 20 at the target location. Once the drainage stent 20 has been properly deployed at the target location, the drainage stent delivery system 10 may then be withdrawn. In some instances, the drainage stent delivery system 10 may also be used to reposition and/or retrieve the drainage stent 20 during a medical procedure.

Some exemplary locking structures for selectively coupling the drainage stent 20 to a component, such as an elongate shaft, of the drainage stent delivery system 10 will now be further described.

FIGS. 3A-3E illustrate the functionality of a first exemplary locking structure for selectively coupling the drainage stent 20 to an elongate shaft of the drainage stent delivery system 10. Although the drainage stent 20 is illustrated as being selectively coupled to the push catheter 14 of the drainage stent delivery system 10, it is understood that in some embodiments the guide catheter 12 may be so configured such that the drainage stent 20 may be selectively coupled to the guide catheter 12, or another elongate shaft, in the manner described with regard to FIGS. 3A-3E.

Figure 3A:
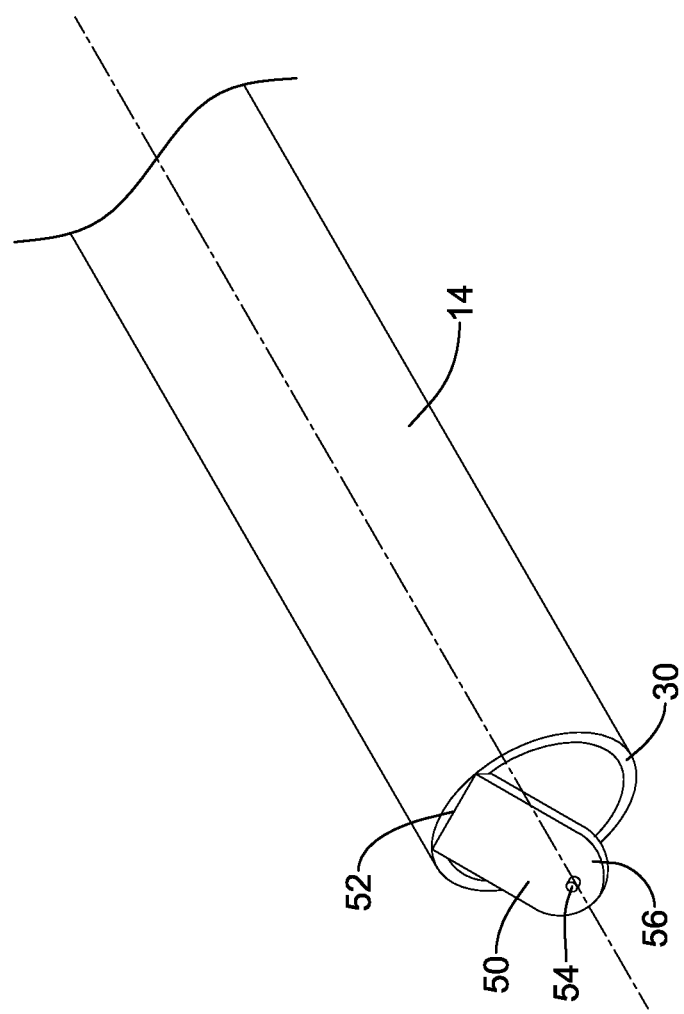
FIGS. 3A-3E illustrate the functionality of an exemplary locking structure for selectively coupling a stent to an elongate shaft of a delivery system.

FIG. 3A shows one possible configuration of the distal end region of the push catheter 14, including a coupling member configured for engagement with the drainage stent 20 to selectively couple the drainage stent 20 to the push catheter 14. The push catheter 14 may include a tab 50 extending distally from the distal end 30 of the elongate tubular member of the push catheter 14. The tab 50 may be attached and/or extend from the tubular wall of the push catheter 14. In some instances, the tab 50 may be a flap 56 hingedly coupled to the tubular wall of the push catheter 14 by a living hinge 52 between the tubular wall and the flap 56, or otherwise deflectable. The tab 50 may include a protuberance 54 or other engagement feature extending from the surface of the tab 50 configured to mate with an opening or other engagement feature of the drainage stent 20. In some instances, the engagement feature may be a compliant and/or non-lubricious material, such as a silicone member, secured to the flap 56 of the tab 50, or the entire tab 50 or portions thereof may be formed of a compliant and/or non-lubricious material, such as silicone or polymeric foam, forming a silicone or foam flap 56 configured to frictionally engage the drainage stent 20. Additionally or alternatively, the flap 56 and/or protuberance 54 of the tab 50 and/or other portion of the tab 50 may include a surface treatment, adhesive or tacky coating or other coating, and/or surface features to further enhance engagement with the drainage stent 20.

Although a single tab 50 is illustrated, in some embodiments the push catheter 14 may include a plurality of tabs 50 similarly arranged at the distal end 30 of the elongate tubular member of the push catheter 14 which collectively act to selectively engage the drainage stent 20 in a similar manner as described herein.

Figure 3B:
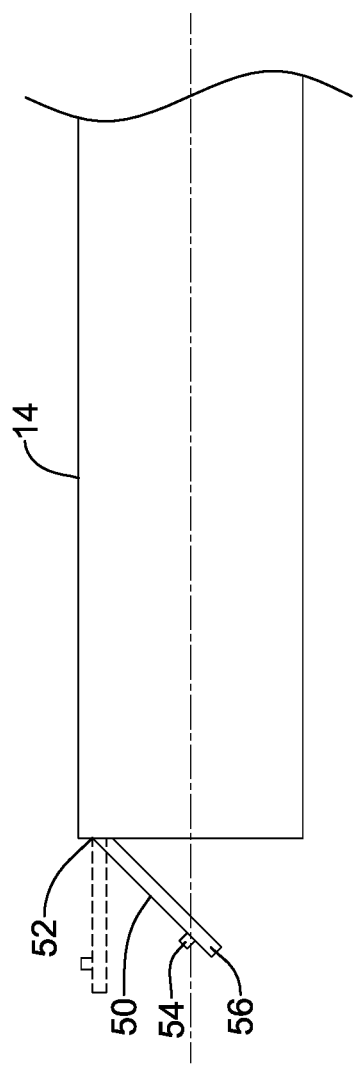

The tab 50 may be configured to move between a first position and a second position. For example, the tab 50 may be configured such that the protuberance 54 is disengaged from the drainage stent 20 when at the first position and engaged with the drainage stent 20 when at the second position. FIG. 3B shows the position of the tab 50 at the first position (solid lines), as well as the position of the tab 50 when at the second position (in phantom lines). As shown in FIG. 3B, the distal end of the tab 50, and thus the protuberance 54, moves toward the central longitudinal axis of the push catheter 14 when the tab 50 is moved from the second position to the first position, or conversely, the distal end of the tab 50, and thus the protuberance 54, moves away from the central longitudinal axis of the push catheter 14 when the tab 50 is moved from the first position to the second position. As shown in FIG. 3B, in some instances the tab 50 may intersect the central longitudinal axis of the push catheter 14 when at the first position and the tab 50 may be generally parallel to the central longitudinal axis of the push catheter 14 when at the second position.

In some instances, the first position may be an equilibrium position of the tab 50. In other words, the tab 50 may be biased toward the first position, thus when an applied force is removed from the tab 50, the tab 50 may automatically revert back to the equilibrium first position. The tab 50 may be deflected toward the second position by applying a force to the tab 50. Thus, when not subjected to an applied force, the tab 50 may be at the first position in which the tab 50 is disengaged from the drainage stent 20.

Figure 3C:
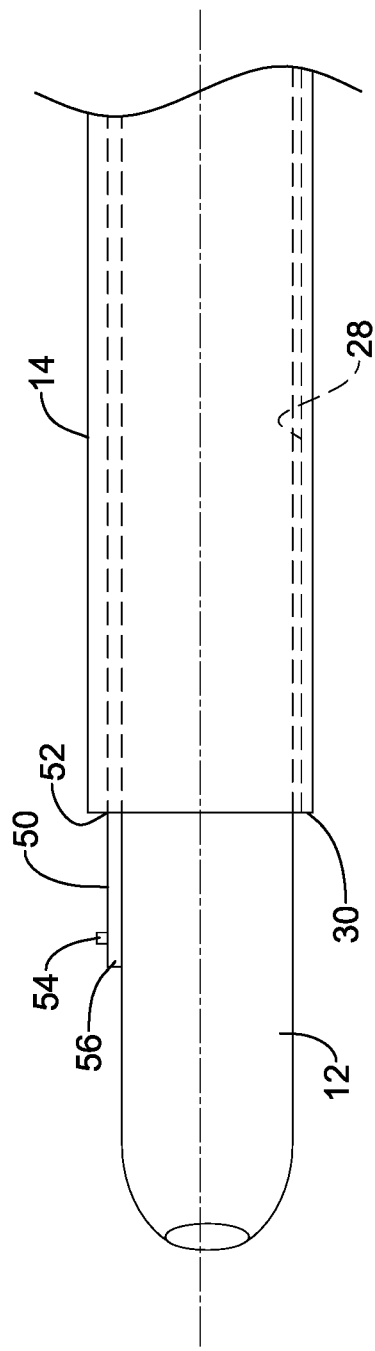

As shown in FIG. 3C, in some instances the tab 50 may be urged to the second position from the first position with the guide catheter 12. For example, the guide catheter 12 may be positioned in the lumen 28 of the push catheter 14 with a distal portion of the guide catheter 12 extending distal of the distal end 30 of the push catheter 14. The guide catheter 12 contacts the tab 50, pushing the tab 50 away from the central longitudinal axis of the push catheter 14 to allow the guide catheter 12 to extend distally of the tab 50. Thus, the guide catheter 12 may apply a force onto the tab 50 to move the tab 50 to the second position from the first position.

Figure 3D:
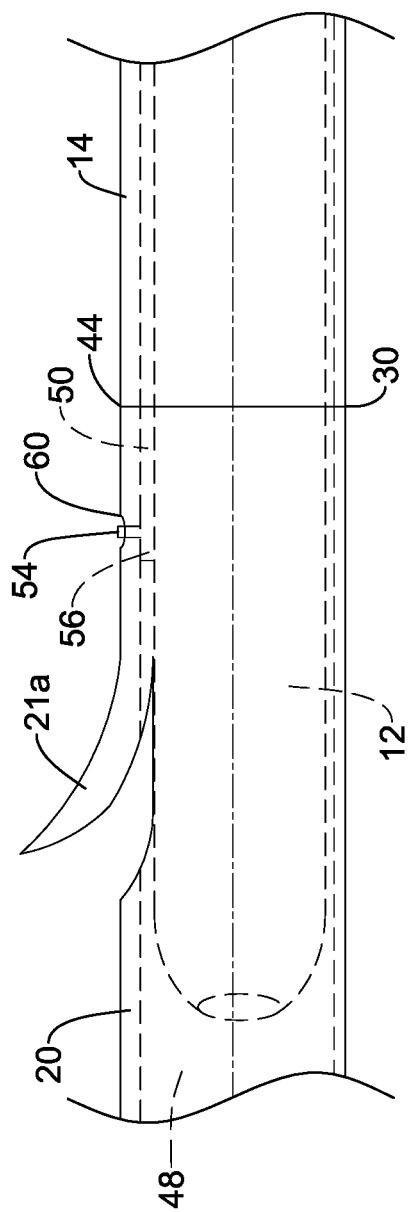
Figure 3E:
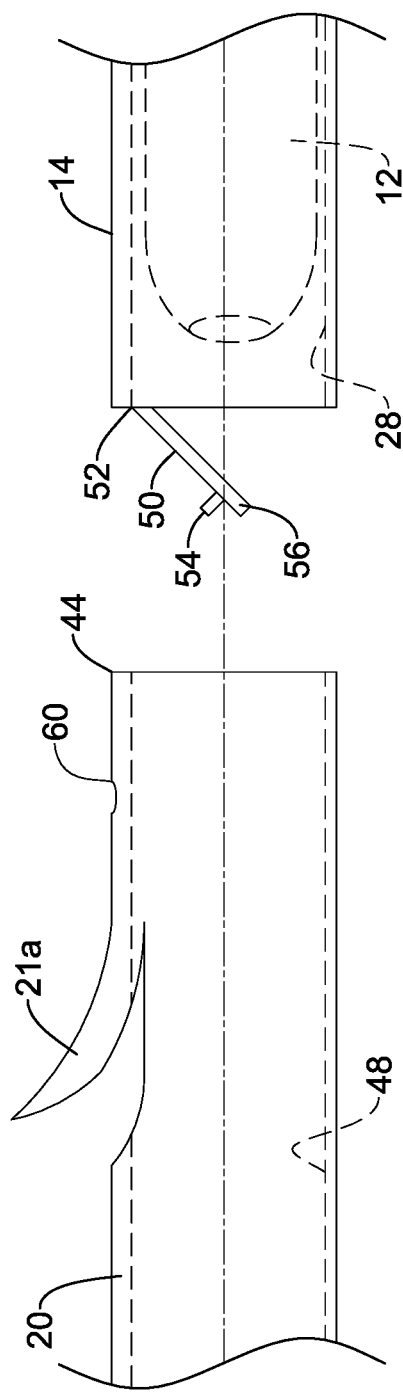

FIGS. 3D and 3E show the drainage stent 20 selectively coupled to and decoupled from the push catheter 14, respectively, by means of the tab 50. As shown in FIG. 3D, the drainage stent 20 may be positioned proximate the distal end 30 of the push catheter 14 with the tab 50 extending into the lumen 48 of the drainage stent 20. With the drainage stent 20 coupled to the push catheter 14, the proximal end 44 of the drainage stent 20 may face or abut the distal end 30 of the push catheter 14. In other embodiments, however, the proximal end 44 of the drainage stent 20 may overlap with the distal end 30 of the push catheter 14. The drainage stent 20 may be selectively coupled to the push catheter 14 by advancing the guide catheter 12 distally into and/or through the lumen 48 of the drainage stent 20 such that the guide catheter 12 urges or deflects the tab 50 away from the central longitudinal axis of the push catheter 14 into engagement with the drainage stent 20. When the tab 50 is urged to the second position the protuberance 54 extending from the flap 56 of the tab 50 may be inserted into an opening 60 extending into and/or through the sidewall of the drainage stent 20, coupling the drainage stent 20 to the push catheter 14. The presence of the guide catheter 12 in the lumen 48 of the drainage stent 20 may prevent the tab 50 from moving back to the first position, and thus may preclude the protuberance 54 from being removed from the opening 60 in the drainage stent 20. It is noted that in some embodiments, the opening 60 and the protuberance 54 may be reversed, such that the tab 50 may include an opening and the drainage stent 20 may include a protuberance which may be selectively positioned in the opening of the tab 50 in a similar manner.

The drainage stent 20 may be decoupled from the push catheter 14 by withdrawing the guide catheter 12 proximally from the lumen 48 of the drainage stent 20, as shown in FIG. 3E. As the guide catheter 12 is withdrawn proximally relative to the drainage stent 20, the guide catheter 12 may be moved out of engagement with the tab 50, allowing the tab 50 to revert to the first position, while the proximal end 44 of the drainage stent 20 abuts the distal end 30 of the push catheter 14, holding the drainage stent 20 stationary relative to the push catheter 14. For instance, the guide catheter 12 may be withdrawn proximally such that the distal end of the guide catheter 12 is proximal of the distal end 30 of the push catheter 14, at which point the tab 50 is no longer constrained by the guide catheter 12 and may automatically move back to its equilibrium first position. As the distal end of the tab 50, and thus the protuberance 54, moves toward the central longitudinal axis of the push catheter 14, the protuberance 54 is removed from the opening 60 in the drainage stent 20, decoupling the drainage stent 20 from the push catheter 14. Once the drainage stent 20 is decoupled from the push catheter 14, the push catheter 14 and/or the guide catheter 12 may be withdrawn from the patient, leaving the drainage stent 20 at the desired location in the lumen.

Figure 4A:
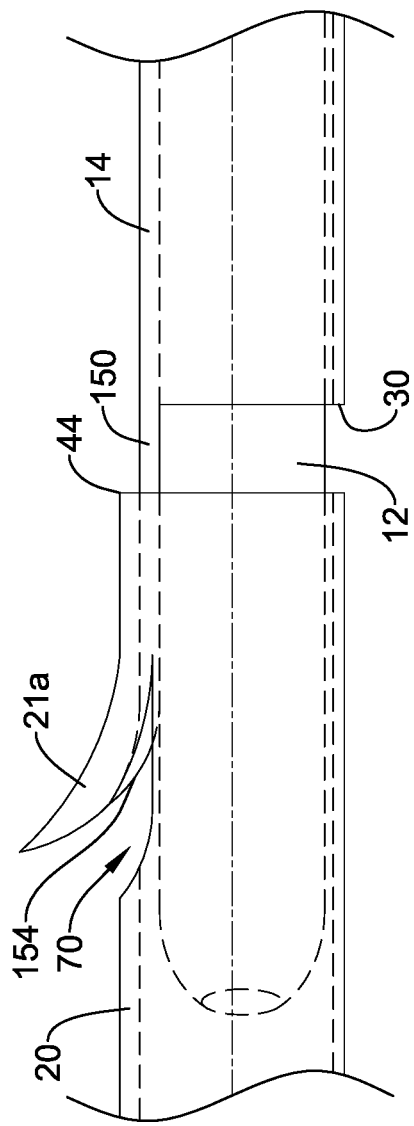
FIGS. 4A and 4B are side views illustrating the functionality of another locking structure for selectively coupling a stent to an elongate shaft of a delivery system.
Figure 4B:
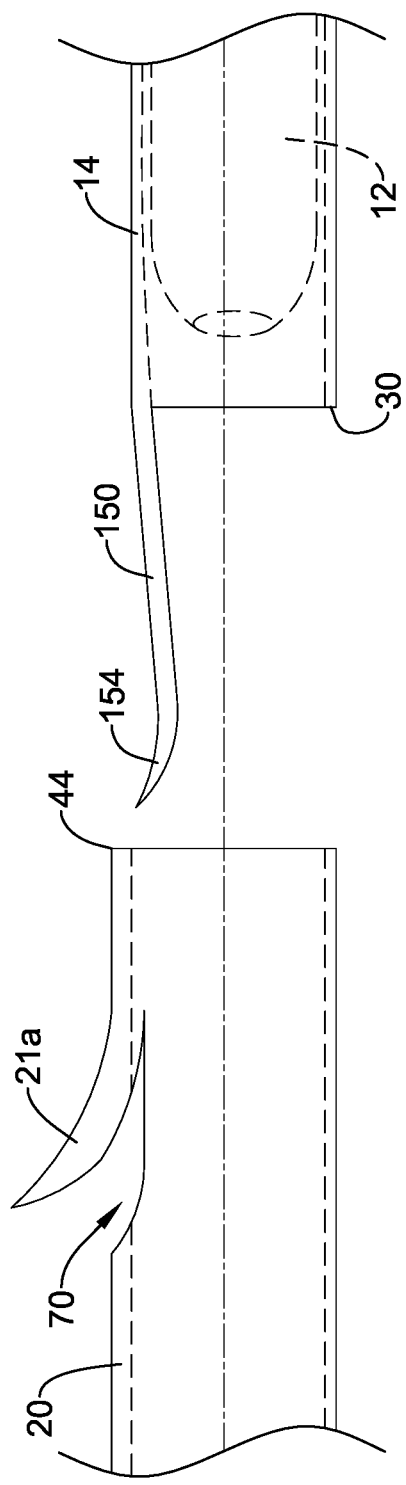

FIGS. 4A and 4B illustrate another exemplary embodiment of the distal end region of the push catheter 14, including a coupling member configured for engagement with the drainage stent 20 to selectively couple the drainage stent 20 to the push catheter 14. Although the drainage stent 20 is illustrated as being selectively coupled to the push catheter 14 of the drainage stent delivery system 10, it is understood that in some embodiments the guide catheter 12 may be so configured such that the drainage stent 20 may be selectively coupled to the guide catheter 12, or another elongate shaft, in the manner described with regard to FIGS. 4A and 4B.

The push catheter 14 may include a tab 150 extending distally from the distal end 30 of the elongate tubular member of the push catheter 14. The tab 150 may be attached and/or extend from the tubular wall of the push catheter 14. In some instances, the tab 150 may be deflectable when a force is applied to the tab 150. The tab 150 may include a curved tip 154 or other engagement feature configured to mate with an opening or other engagement feature of the drainage stent 20. The curved tip 154 may curve radially outward away from the central longitudinal axis of the push catheter 14. It is noted that in some embodiments the tab 150 need not have a curved tip 154, but rather may be configured to interlock with or frictionally engage a portion of the drainage stent 20. For example, the tab 150 may form an interference fit with a hole formed in the drainage stent 20, or the tab 150 may be formed of a compliant material such that when the tab 150, which may be sized slightly larger than the hole, is inserted into the hole in the drainage stent 20 the tab 150 fills the hole. In some instances, the tab 150 may be notched or barbed to interlock with a feature of the drainage stent 20.

Although a single tab 150 is illustrated, in some embodiments the push catheter 14 may include a plurality of tabs 150 similarly arranged at the distal end 30 of the elongate tubular member of the push catheter 14 which collectively act to selectively engage the drainage stent 20 in a similar manner as described herein.

The tab 150 may be configured to move between a first position and a second position. For example, the tab 150 may be configured such that the curved tip 154 is disengaged from the drainage stent 20 when at the first position and engaged with the drainage stent 20 when at the second position. FIG. 4A shows the position of the tab 150 at the first position, while FIG. 4B shows the position of the tab 150 at the second position. As can be understood from FIGS. 4A and 4B, the distal end of the tab 150, and thus the curved tip 154, moves toward the central longitudinal axis of the push catheter 14 when the tab 150 is moved from the second position to the first position, or conversely, the distal end of the tab 150, and thus the curved tip 154, moves away from the central longitudinal axis of the push catheter 14 when the tab 150 is moved from the first position to the second position.

In some instances, the first position may be an equilibrium position of the tab 150. In other words, the tab 150 may be biased toward the first position, thus when an applied force is removed from the tab 150, the tab 150 may automatically revert back to the equilibrium first position. The tab 150 may be deflected toward the second position by applying a force to the tab 150. Thus, when not subjected to an applied force, the tab 150 may be at the first position in which the tab 150 is disengaged from the drainage stent 20.

Similar to the configuration discussed above, in some instances the tab 150 may be urged to the second position from the first position with the guide catheter 12. For example, the guide catheter 12 may be positioned in the lumen 28 of the push catheter 14 with a distal portion of the guide catheter 12 extending distal of the distal end 30 of the push catheter 14. The guide catheter 12 contacts the tab 150, pushing the tab 150 away from the central longitudinal axis of the push catheter 14 to allow the guide catheter 12 to extend distally of the tab 150. Thus, the guide catheter 12 may apply a force onto the tab 150 to move the tab 150 to the second position from the first position.

FIGS. 4A and 4B show the drainage stent 20 selectively coupled to and decoupled from the push catheter 14, respectively, by means of the tab 150. As shown in FIG. 4A, the drainage stent 20 may be positioned proximate the distal end 30 of the push catheter 14 with the tab 150 extending into the lumen 48 of the drainage stent 20. With the drainage stent 20 coupled to the push catheter 14, the proximal end 44 of the drainage stent 20 may face or abut the distal end 30 of the push catheter 14. In other embodiments, however, the proximal end 44 of the drainage stent 20 may overlap with the distal end 30 of the push catheter 14. The drainage stent 20 may be selectively coupled to the push catheter 14 by advancing the guide catheter 12 distally into and/or through the lumen 48 of the drainage stent 20 such that the guide catheter 12 urges or deflects the tab 150 away from the central longitudinal axis of the push catheter 14 into engagement with the drainage stent 20. When the tab 150 is urged to the second position the curved tip 154 of the tab 150 may be inserted into an opening 70 in the sidewall of the drainage stent 20 formed consequent the barb 21a being cut from the tubular wall of the drainage stent 20, coupling the drainage stent 20 to the push catheter 14. The presence of the guide catheter 12 in the lumen 48 of the drainage stent 20 may prevent the tab 150 from moving back to the first position, and thus may preclude the curved tip 154 from being removed from the opening 70 in the drainage stent 20. It is noted that in some embodiments, the drainage stent 20 may include an opening distinct from the opening 70 into which the curved tip 154 of the tab 150 may extend into to couple the drainage stent 20 to the push catheter 14.

The drainage stent 20 may be decoupled from the push catheter 14 by withdrawing the guide catheter 12 proximally from the lumen 48 of the drainage stent 20, as shown in FIG. 4B. As the guide catheter 12 is withdrawn proximally relative to the drainage stent 20, the guide catheter 12 may be moved out of engagement with the tab 150, allowing the tab 150 to revert to the first position, while holding the drainage stent 20 stationary relative to the push catheter 14. For instance, the guide catheter 12 may be withdrawn proximally such that the distal end of the guide catheter 12 is proximal of the distal end 30 of the push catheter 14, at which point the tab 150 is no longer constrained by the guide catheter 12 and may automatically move back to its equilibrium first position. As the distal end of the tab 150, and thus the curved tip 154, moves toward the central longitudinal axis of the push catheter 14, the curved tip 154 is removed from the opening 70 in the drainage stent 20, decoupling the drainage stent 20 from the push catheter 14. Once the drainage stent 20 is decoupled from the push catheter 14, the push catheter 14 and/or the guide catheter 12 may be withdrawn from the patient, leaving the drainage stent 20 at the desired location in the lumen.

Figure 5A:
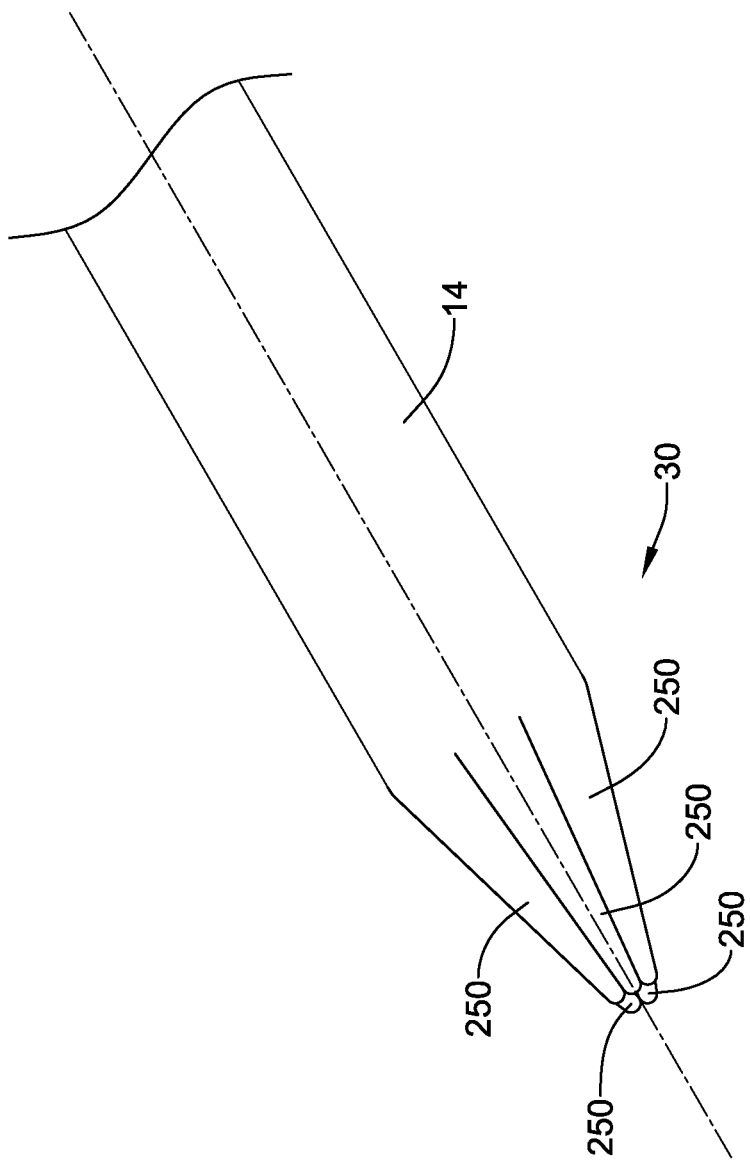
FIGS. 5A and 5B are perspective views illustrating the distal end of an embodiment of an elongate member configured for selectively coupling to a stent for delivery.
Figure 5B:
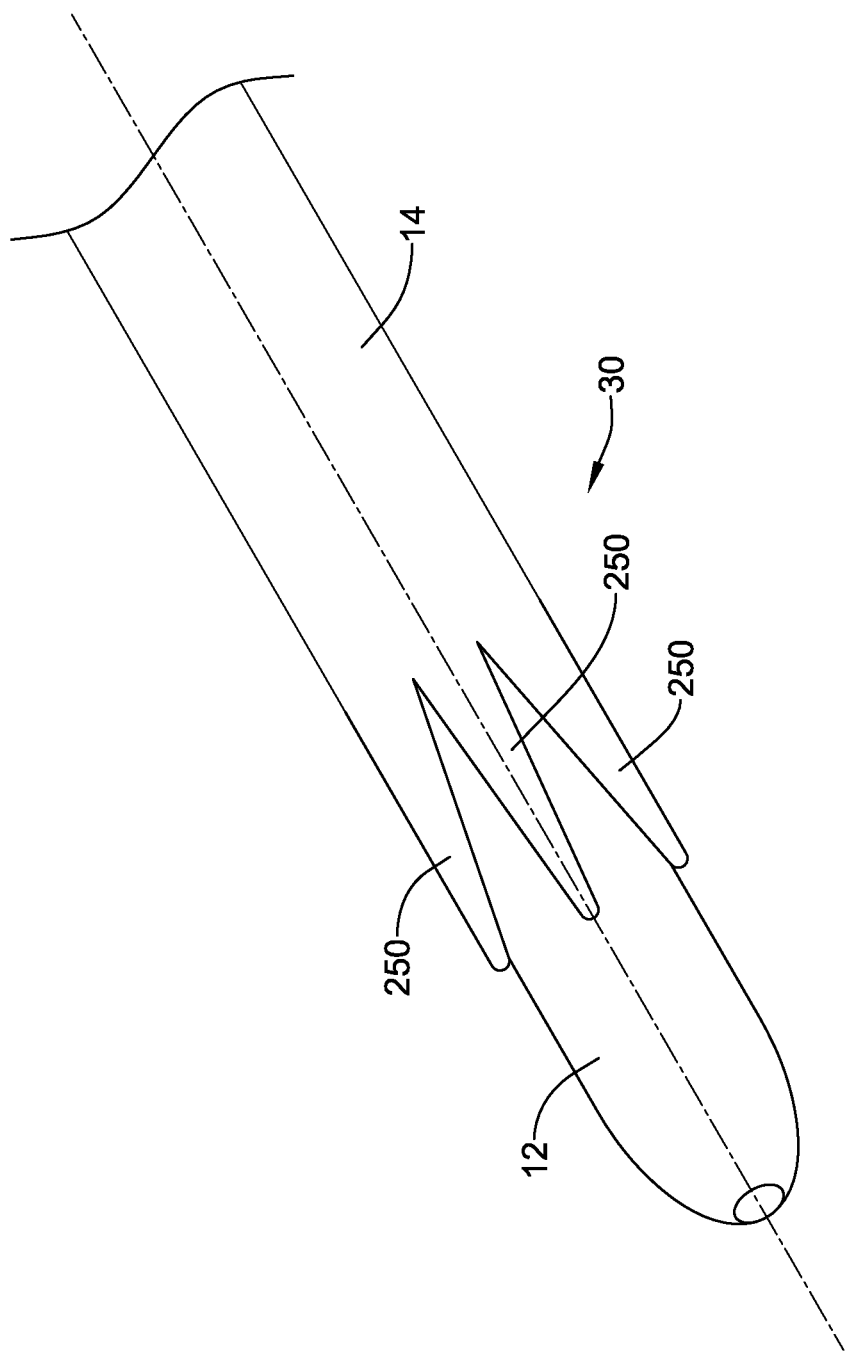
Figure 5C:
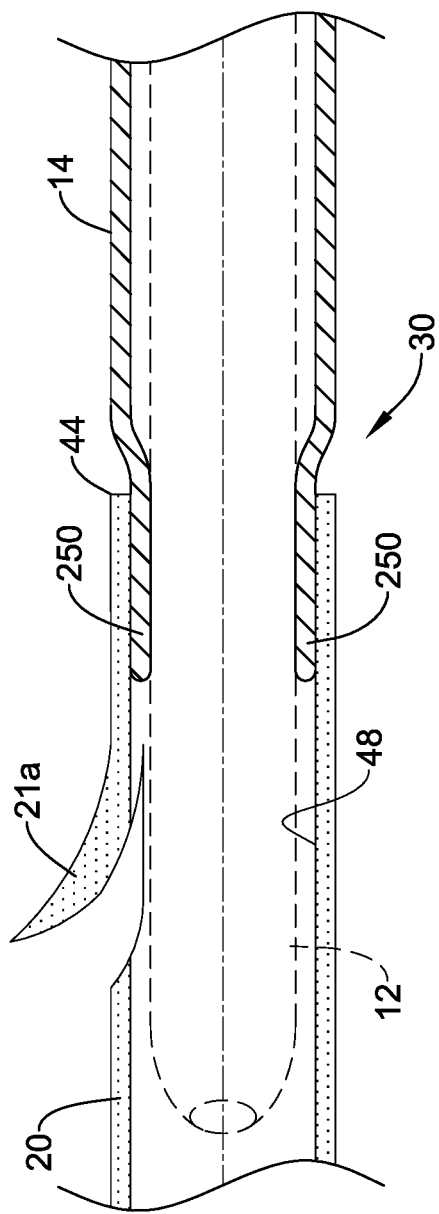
FIGS. 5C and 5D are cross-sectional views illustrating the functionality of the locking structure of FIGS. 5A and 5B for selectively coupling a stent to an elongate shaft of a delivery system.
Figure 5D:
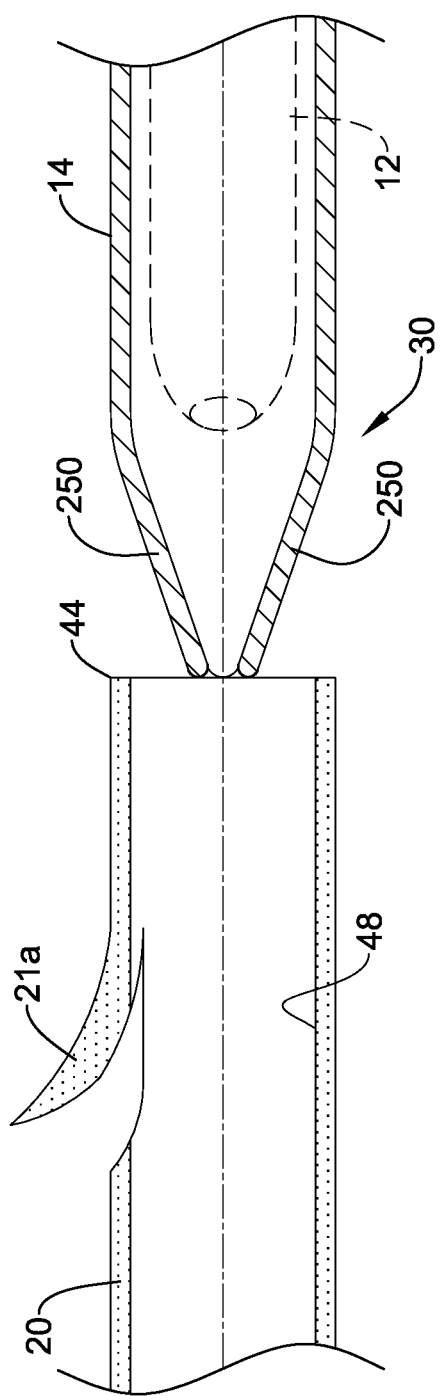

FIGS. 5A and 5B illustrate another exemplary embodiment of the distal end region of the push catheter 14, including a coupling member configured for engagement with the drainage stent 20 to selectively couple the drainage stent 20 to the push catheter 14 as shown in FIGS. 5C and 5D. Although the drainage stent 20 is illustrated as being selectively coupled to the push catheter 14 of the drainage stent delivery system 10, it is understood that in some embodiments the guide catheter 12 may be so configured such that the drainage stent 20 may be selectively coupled to the guide catheter 12, or another elongate shaft, in the manner described with regard to FIGS. 5C and 5D.

The push catheter 14 may include a plurality of tabs 250 radially arranged and extending distally from the distal end 30 of the elongate tubular member of the push catheter 14. The tabs 250 may be symmetrically or asymmetrically arranged around the circumference of the elongate tubular member of the push catheter 14, for example. The tabs 250 may be attached and/or extend from the tubular wall of the push catheter 14. In some instances, the tabs 250 may be deflectable when a force is applied to the tabs 250.

The tabs 250 may be configured to move between a first position and a second position. For example, the tabs 250 may be configured such that the tabs 250 are disengaged from the drainage stent 20 when at the first position and engaged with the drainage stent 20 when at the second position. FIG. 5A shows the position of the tabs 250 at the first position, while FIG. 5B shows the position of the tabs 250 at the second position with the guide catheter 12 deflecting the tabs 250 radially outward. In the first position, the tabs 250 may taper in a distal direction toward the central longitudinal axis of the push catheter 14, thus forming a distally tapered tip on the push catheter 14 formed of a plurality of tabs 250 radially arranged. As can be understood from FIGS. 5A and 5B, the distal ends of the tabs 250 move toward the central longitudinal axis of the push catheter 14 when the tabs 250 are moved from the second position to the first position, or conversely, the distal ends of the tabs 250 move away from the central longitudinal axis of the push catheter 14 when the tabs 250 are moved from the first position to the second position.

In some instances, the first position may be an equilibrium position of the tabs 250. In other words, the tabs 250 may be biased toward the first position, thus when an applied force is removed from the tabs 250, the tabs 250 may automatically revert back to the equilibrium first position. The tabs 250 may be deflected toward the second position by applying a force to the tabs 250. Thus, when not subjected to an applied force, the tabs 250 may be at the first position in which the tabs 250 are disengaged from the drainage stent 20.

Similar to the configuration discussed above, in some instances the tabs 250 may be urged to the second position from the first position with the guide catheter 12. For example, the guide catheter 12 may be positioned in the lumen 28 of the push catheter 14 with a distal portion of the guide catheter 12 extending distal of the distal end 30 of the push catheter 14. The guide catheter 12 contacts the tabs 250, pushing the tabs 250 away from the central longitudinal axis of the push catheter 14 to allow the guide catheter 12 to extend distally of the tabs 250. Thus, the guide catheter 12 may apply a force onto the tabs 250 to move the tabs 250 to the second position from the first position.

FIGS. 5C and 5D show the drainage stent 20 selectively coupled to and decoupled from the push catheter 14, respectively, by means of the tabs 250. As shown in FIG. 5C, the drainage stent 20 may be positioned proximate the distal end 30 of the push catheter 14 with the tabs 250 extending into the lumen 48 of the drainage stent 20. The drainage stent 20 may be selectively coupled to the push catheter 14 by advancing the guide catheter 12 distally into and/or through the lumen 48 of the drainage stent 20 such that the guide catheter 12 urges or deflects the tabs 250 away from the central longitudinal axis of the push catheter 14 into engagement with the drainage stent 20. When the tabs 250 are urged to the second position the tabs 250 may frictionally engage an inner surface of the drainage stent 20 and/or interlock with a feature of the drainage stent 20, coupling the drainage stent 20 to the push catheter 14. The presence of the guide catheter 12 in the lumen 48 of the drainage stent 20 may prevent the tabs 250 from moving back to the first position, and thus may maintain the tabs 250 in engagement with the drainage stent 20. It is noted that in some embodiments, the drainage stent 20 may include one or more openings or grooves into which the tabs 250 are engaged with.

The drainage stent 20 may be decoupled from the push catheter 14 by withdrawing the guide catheter 12 proximally from the lumen 48 of the drainage stent 20, as shown in FIG. 5D. As the guide catheter 12 is withdrawn proximally relative to the drainage stent 20, the guide catheter 12 may be moved out of engagement with the tabs 250, allowing the tabs 250 to revert to the first position, while holding the drainage stent 20 stationary relative to the push catheter 14. For instance, the guide catheter 12 may be withdrawn proximally such that the distal end of the guide catheter 12 is proximal of the distal end 30 of the push catheter 14, at which point the tabs 250 are no longer constrained by the guide catheter 12 and may automatically move back to their equilibrium first position. As the distal ends of the tabs 250 move toward the central longitudinal axis of the push catheter 14, the tabs 250 are disengaged from the drainage stent 20, decoupling the drainage stent 20 from the push catheter 14. Once the drainage stent 20 is decoupled from the push catheter 14, the push catheter 14 and/or the guide catheter 12 may be withdrawn from the patient, leaving the drainage stent 20 at the desired location in the lumen.

Figure 6A:
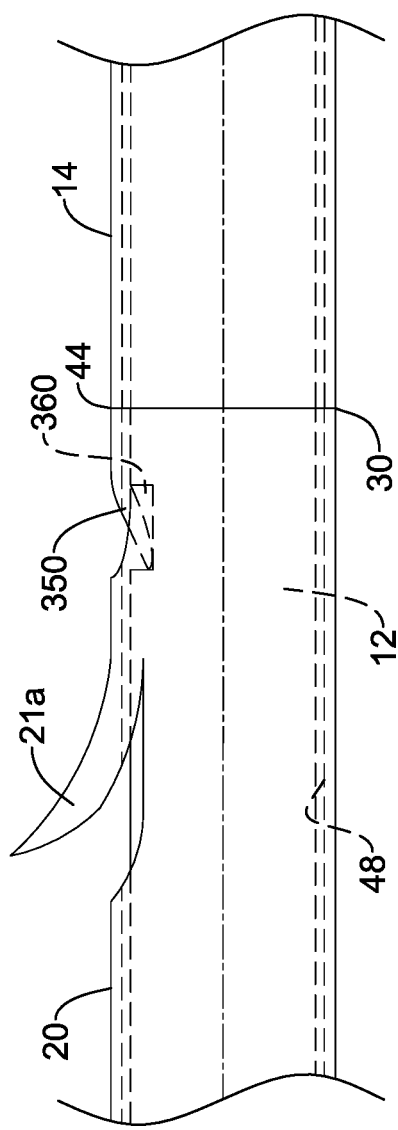
FIGS. 6A and 6B are side views illustrating the functionality of another locking structure for selectively coupling a stent to an elongate shaft of a delivery system.
Figure 6B:
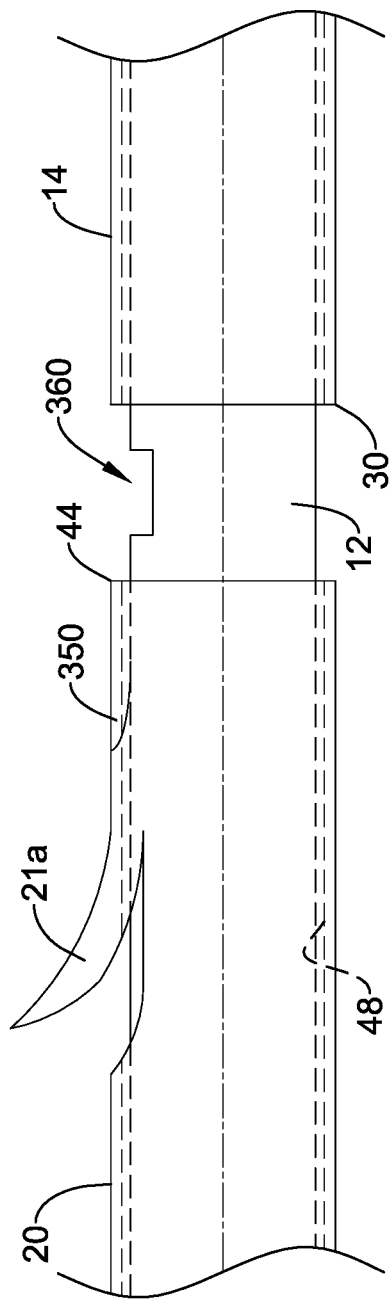

FIGS. 6A and 6B illustrate another exemplary embodiment of the drainage stent 20 selectively coupled with the guide catheter 12. Although the drainage stent 20 is illustrated as being selectively coupled to the guide catheter 12 of the drainage stent delivery system 10, it is understood that in some embodiments the push catheter 14 may be so configured such that the drainage stent 20 may be selectively coupled to the push catheter 14, or another elongate shaft, in the manner described with regard to FIGS. 6A and 6B.

The drainage stent 20 may include a tab 350 extending radially inward from the tubular wall of the drainage stent 20 into the lumen 48 of the drainage stent 20. The tab 350 may be cut from the tubular wall of the drainage stent 20, thus forming a unitary structure with the tubular wall of the drainage stent 20. In some instances, the tab 350 may be deflectable when a force is applied to the tab 350. The tab 350 may be configured to mate with an opening or other engagement feature of the guide catheter 12.

Although a single tab 350 is illustrated, in some embodiments the drainage stent 20 may include a plurality of tabs 350 similarly arranged around the circumference of the drainage stent 20 which collectively act to selectively engage the guide catheter 12 in a similar manner as described herein.

The tab 350 may be configured to move between a first position and a second position. For example, the tab 350 may be configured such that the tab 350 is engaged with the guide catheter 12 when at the first position and disengaged from the guide catheter 12 when at the second position. FIG. 6A shows the position of the tab 350 at the first position, while FIG. 6B shows the position of the tab 350 at the second position. As can be understood from FIGS. 6A and 6B, the free end of the tab 350 moves toward the central longitudinal axis of the guide catheter 12 when the tab 350 moves from the second position to the first position, or conversely, the free end of the tab 350 moves away from the central longitudinal axis of the guide catheter 12 when the tab 350 moves from the first position to the second position.

In some instances, the first position may be an equilibrium position of the tab 350. In other words, the tab 350 may be biased toward the first position, thus when an applied force is removed from the tab 350, the tab 350 may automatically revert back to the equilibrium first position. The tab 350 may be deflected toward the second position by applying a force to the tab 350. Thus, when not subjected to an applied force, the tab 350 may move back toward the first position.

The guide catheter 12 may include an engagement feature, such as an opening 360 formed in the guide catheter 12. The opening 360 may be a groove, channel, blind hole, through hole, or other feature configured to receive and engage with the tab 350. The opening 360 may be formed in or through the tubular member of the guide catheter 12. The tab 350 may be positioned in the opening 360 to lock the drainage stent 20 to the guide catheter 12.

In some instances the tab 350 may be urged to the second position from the first position through movement of the guide catheter 12 while holding the drainage stent 20 stationary relative to the push catheter 14. For example, the guide catheter 12 may be positioned in the lumen 28 of the push catheter 14 with a distal portion of the guide catheter 12 extending distal of the distal end 30 of the push catheter 14 and into or through the lumen 48 of the drainage stent 20. The guide catheter 12 may contact the tab 350, pushing the tab 350 away from the central longitudinal axis of the guide catheter 12 to allow the guide catheter 12 to extend distally of the tab 350. Thus, the guide catheter 12 may apply a force onto the tab 350 to move the tab 350 to the second position from the first position. As the guide catheter 12 is moved further distally relative to the drainage stent 20, the tab 350 may become aligned with the opening 360 and thus engage with the opening 360 as the tab 350 moves toward the first position.

FIGS. 6A and 6B show the drainage stent 20 selectively coupled to and decoupled from the guide catheter 12, respectively, by means of engagement of the tab 350 with the opening 360. As shown in FIG. 6A, the drainage stent 20 may be positioned proximate the distal end 30 of the push catheter 14 with the tab 350 extending into the opening 360. With the drainage stent 20 coupled to the guide catheter 12, the proximal end 44 of the drainage stent 20 may face or abut the distal end 30 of the push catheter 14. In other embodiments, however, the proximal end 44 of the drainage stent 20 may overlap with the distal end 30 of the push catheter 14. The drainage stent 20 may be selectively coupled to the guide catheter 12 by advancing the guide catheter 12 distally into and/or through the lumen 48 of the drainage stent 20 until the tab 350 extends into the opening 360 of the guide catheter 12.

The drainage stent 20 may be decoupled from the guide catheter 12 by movement of the guide catheter 12 relative to the drainage stent 20. For example, rotational and/or longitudinal movement of the guide catheter 12 may disengage the tab 350 from the opening 360. For instance, in some instances the guide catheter 12 may be rotated to deflect the tab 350 to the second position and thus remove the tab 350 from the opening 360. In other instances, the guide catheter 12 may be moved longitudinally (e.g., proximally and/or distally) relative to the drainage stent 20 to deflect the tab 350 to the second position and thus remove the tab 350 from the opening 360. In some instances, the guide catheter 12 may initially be moved distally relative to the drainage stent 20 until the tab 350 is deflected out of engagement with the opening 360. The guide catheter 12 may then be rotated to move the opening 360 away from the tab 350. Thus, when the guide catheter 12 is subsequently withdrawn proximally, the tab 350 will not re-engage with the opening 360. With the tab 350 disengaged from the opening 360, the guide catheter 12 may be withdrawn proximally such that the distal end of the guide catheter 12 is proximal of the distal end 30 of the push catheter 14, at which point the drainage stent 20 is decoupled from the guide catheter 12. Once the drainage stent 20 is decoupled from the guide catheter 12, the push catheter 14 and/or the guide catheter 12 may be withdrawn from the patient, leaving the drainage stent 20 at the desired location in the lumen.

Figure 7A:
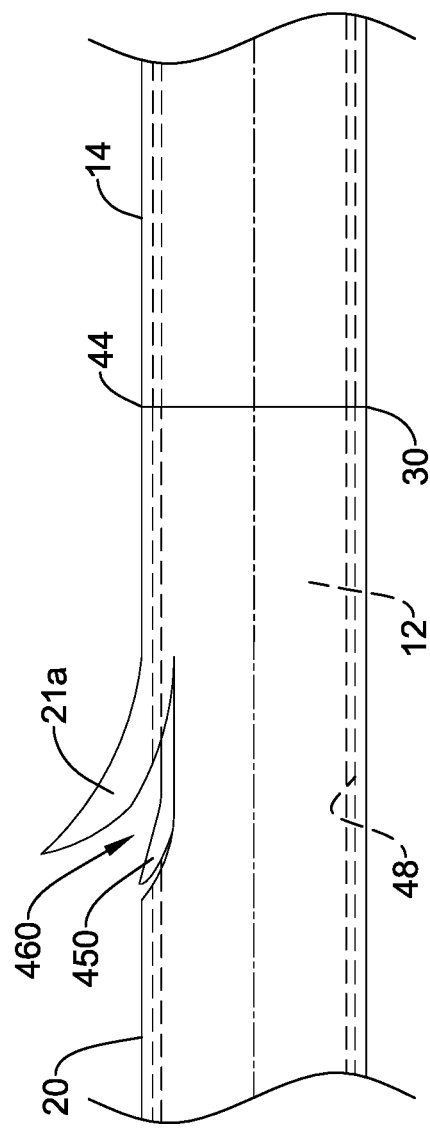
FIGS. 7A and 7B are side views illustrating the functionality of another locking structure for selectively coupling a stent to an elongate shaft of a delivery system.
Figure 7B:
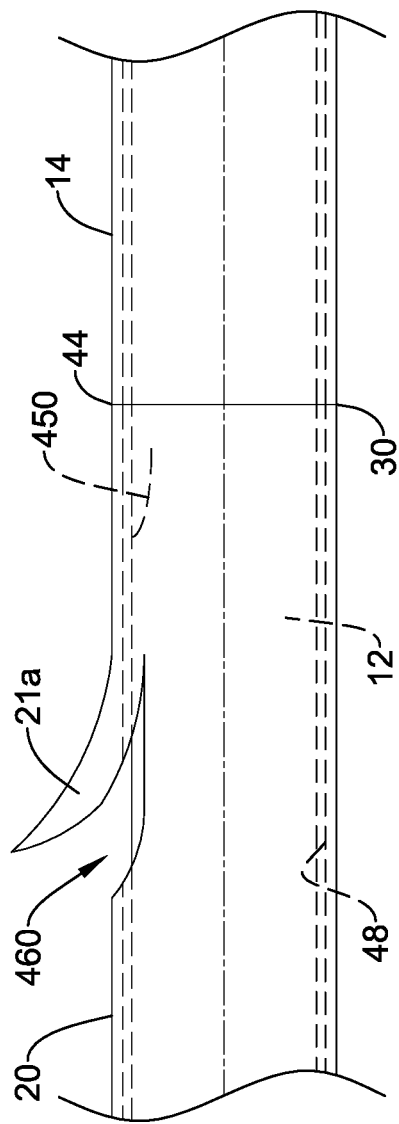

FIGS. 7A and 7B illustrate another exemplary embodiment of the drainage stent 20 selectively coupled with the guide catheter 12. Although the drainage stent 20 is illustrated as being selectively coupled to the guide catheter 12 of the drainage stent delivery system 10, it is understood that in some embodiments the push catheter 14 may be so configured such that the drainage stent 20 may be selectively coupled to the push catheter 14, or another elongate shaft, in the manner described with regard to FIGS. 7A and 7B.

Similar to the embodiment described above, the drainage stent 20 may be selectively coupled to the guide catheter 12 through engagement of a tab 450 with an opening 460. However, in this embodiment, the guide catheter 12 may include the tab 450 and the drainage stent 20 may include the opening 460 into which the tab 450 extends. The tab 450 may extend radially outward from the tubular wall of the guide catheter 12. In some instances, the tab 450 may be cut from the tubular wall of the guide catheter 12, thus forming a unitary structure with the tubular wall of the guide catheter 12. In some instances, the tab 450 may be deflectable when a force is applied to the tab 450. The tab 450 may be configured to mate with an opening or other engagement feature of the drainage stent 20.

Although a single tab 450 is illustrated, in some embodiments the guide catheter 12 may include a plurality of tabs 450 similarly arranged around the elongate tubular member of the guide catheter 12 which collectively act to selectively engage the drainage stent 20 in a similar manner as described herein.

The tab 450 may be configured to move between a first position and a second position. For example, the tab 450 may be configured such that the tab 450 is engaged with the opening 460 of the drainage stent 20 when at the first position and disengaged from the opening 460 of the drainage stent 20 when at the second position. FIG. 7A shows the position of the tab 450 at the first position, while FIG. 7B shows the position of the tab 450 at the second position. As can be understood from FIGS. 7A and 7B, the free end of the tab 450 moves away the central longitudinal axis of the guide catheter 12 when the tab 450 moves from the second position to the first position, or conversely, the free end of the tab 450 moves toward from the central longitudinal axis of the guide catheter 12 when the tab 450 moves from the first position to the second position.

In some instances, the first position may be an equilibrium position of the tab 450. In other words, the tab 450 may be biased toward the first position, thus when an applied force is removed from the tab 450, the tab 450 may automatically revert back to the equilibrium first position. The tab 450 may be deflected toward the second position by applying a force to the tab 450. Thus, when not subjected to an applied force, the tab 450 may move back toward the first position.

The drainage stent 20 may include an engagement feature, such as an opening 460 formed in the drainage stent 20. The opening 460 may be a groove, channel, blind hole, through hole, or other feature configured to receive and engage with the tab 450. The opening 460 may be formed in or through the tubular member of the drainage stent 20. In some instances the opening 460 may be formed in the sidewall of the drainage stent 20 consequent the barb 21a being cut from the tubular wall of the drainage stent 20. The tab 450 may be positioned in the opening 460 to lock the drainage stent 20 to the guide catheter 12.

In some instances the tab 450 may be urged to the second position from the first position through movement of the guide catheter 12. For example, the guide catheter 12 may be positioned in the lumen 28 of the push catheter 14 with a distal portion of the guide catheter 12 extending distal of the distal end 30 of the push catheter 14 and into or through the lumen 48 of the drainage stent 20. The drainage stent 20 may contact the tab 450, pushing the tab 450 toward the central longitudinal axis of the guide catheter 12 to allow the guide catheter 12 to extend distally into the lumen 48 of the drainage stent 20. Thus, the drainage stent 20 may apply a force onto the tab 450 to move the tab 450 to the second position from the first position. As the guide catheter 12 is moved further distally relative to the drainage stent 20, the tab 450 may become aligned with the opening 460 and thus engage with the opening 460 as the tab 450 moves toward the first position.

FIGS. 7A and 7B show the drainage stent 20 selectively coupled to and decoupled from the guide catheter 12, respectively, by means of engagement of the tab 450 with the opening 460. As shown in FIG. 7A, the drainage stent 20 may be positioned proximate the distal end 30 of the push catheter 14 with the tab 450 extending into the opening 460. With the drainage stent 20 coupled to the guide catheter 12, the proximal end 44 of the drainage stent 20 may face or abut the distal end 30 of the push catheter 14. In other embodiments, however, the proximal end 44 of the drainage stent 20 may overlap with the distal end 30 of the push catheter 14. The drainage stent 20 may be selectively coupled to the guide catheter 12 by advancing the guide catheter 12 distally into and/or through the lumen 48 of the drainage stent 20 until the tab 450 extends into the opening 460 of the drainage stent 20.

The drainage stent 20 may be decoupled from the guide catheter 12 by movement of the guide catheter 12 relative to the drainage stent 20 while holding the drainage stent 20 stationary relative to the push catheter 14. For example, rotational and/or longitudinal movement of the guide catheter 12 may disengage the tab 450 from the opening 460. For instance, in some instances the guide catheter 12 may be rotated to deflect the tab 450 to the second position and thus remove the tab 450 from the opening 460. In other instances, the guide catheter 12 may be moved longitudinally (e.g., proximally and/or distally) relative to the drainage stent 20 to deflect the tab 450 to the second position and thus remove the tab 450 from the opening 460. In some instances, the guide catheter 12 may initially be moved distally relative to the drainage stent 20 until the tab 450 is deflected out of engagement with the opening 460. The guide catheter 12 may then be rotated to move the tab 450 away from the opening 460. Thus, when the guide catheter 12 is subsequently withdrawn proximally, the tab 450 will not re-engage with the opening 460. With the tab 450 disengaged from the opening 460, the guide catheter 12 may be withdrawn proximally such that the distal end of the guide catheter 12 is proximal of the distal end 30 of the push catheter 14, at which point the drainage stent 20 is decoupled from the guide catheter 12. Once the drainage stent 20 is decoupled from the guide catheter 12, the push catheter 14 and/or the guide catheter 12 may be withdrawn from the patient, leaving the drainage stent 20 at the desired location in the lumen.

Figure 8A:
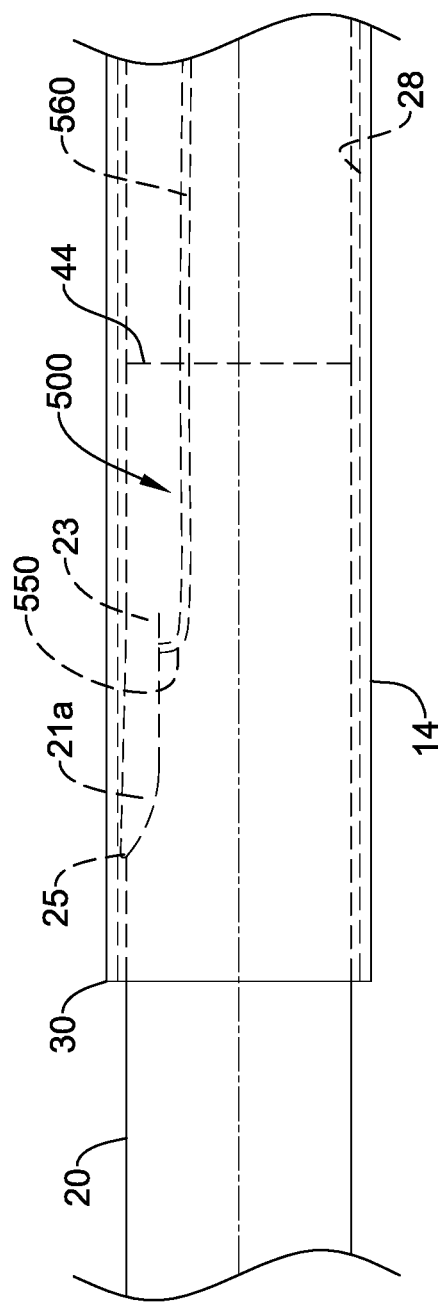
FIGS. 8A-8C illustrate the functionality of yet another locking structure for selectively coupling a stent to an elongate shaft of a delivery system.
Figure 8B:
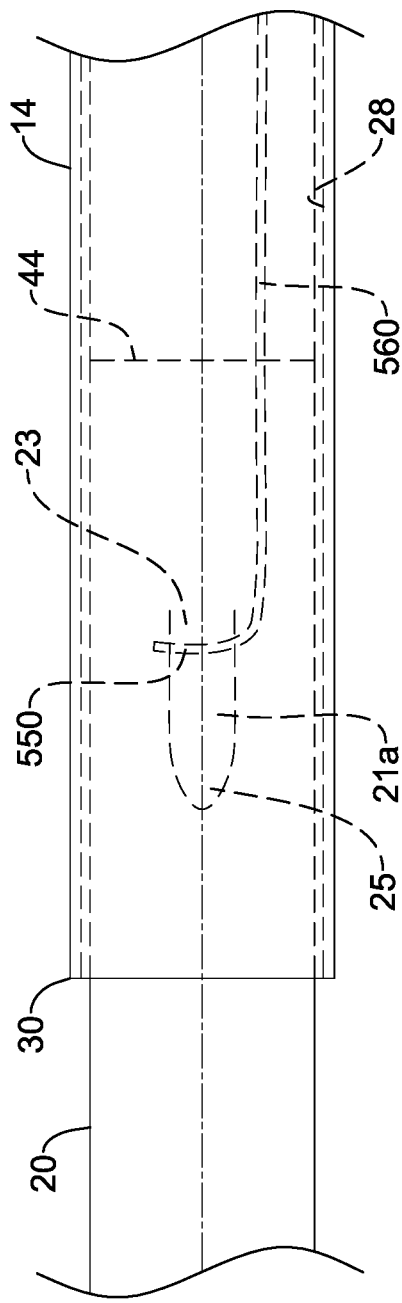
Figure 8C:
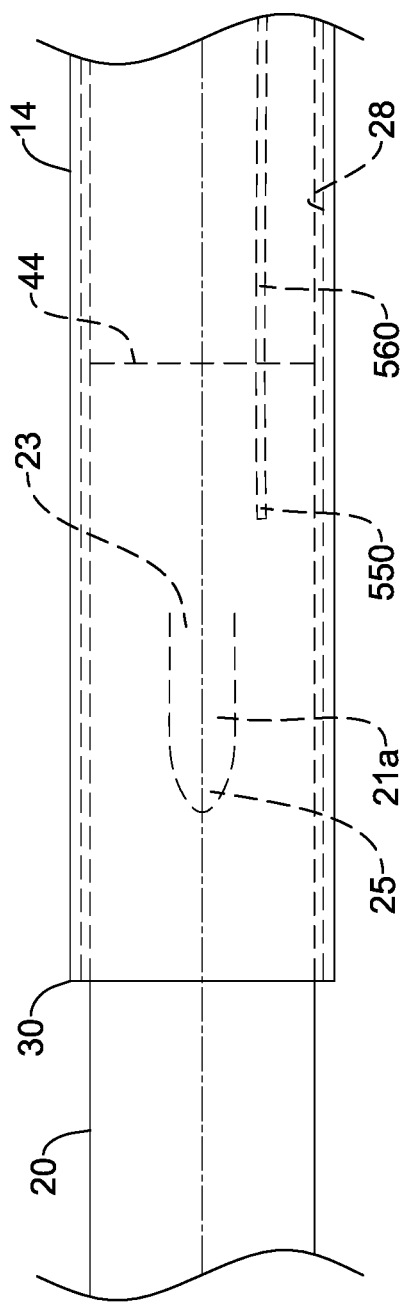

FIGS. 8A-8C illustrate yet another exemplary embodiment of selectively coupling the drainage stent 20 to the drainage stent delivery system 10. As shown in FIG. 8A, a distal portion of the push catheter 14 may extend distally over a proximal portion of the drainage stent 20 such that the distal end 30 of the push catheter 14 is distal of the proximal end 44 of the drainage stent 20. The push catheter 14 may extend sufficiently distally such that at least the proximal portion of the drainage stent 20 including the proximal barb 21a of the drainage stent 20 is disposed within the lumen 28 of the push catheter 14.

The drainage stent delivery system 10 may include a coupling mechanism 500 for selectively coupling the drainage stent 20 to the drainage stent delivery system 10. The coupling mechanism 500 may include an engagement member 550, such as a hook or tab, for engaging with the barb 21a of the drainage stent 20. The coupling mechanism 500 may also include a pull wire 560, or other actuatable feature, extending proximally from the engagement member 550 which an operator may manipulate to selectively disengage the engagement member 550 from the barb 21a. In some embodiments, the pull wire 560, or an extension thereof, may extend proximally to the handle assembly 16, and thus be accessible to the medical personnel external of a patient during a medical procedure to effect actuation of the pull wire 560 and thus disengagement of the engagement member 550 from the barb 21a of the drainage stent 20.

As shown in FIGS. 8A and 8B, in a first position in which the drainage stent 20 is coupled to the push catheter 14, the engagement member 550 (shown as a hook or tab) is positioned across the barb 21a, between the flap of the barb 21a and the tubular portion of the drainage stent 20. The proximal barb 21a, may extend distally from a base 23 of the barb 21a connected to the tubular portion of the drainage stent 20 to a distal free tip 25 of the barb 21a. Thus, the base 23 of the barb 21a, where the barb 21a is connected to the tubular portion of the drainage stent 20, is located proximal of the engagement member 550, with the engagement member 550 positioned radially inward of the flap of the barb 21a.

In order to decouple the drainage stent 20 from the push catheter 14, the pull wire 560 may be withdrawn proximally relative to the drainage stent 20, as shown in FIG. 8C. As the pull wire 560 is pulled proximally, the engagement member 550 may deflect (e.g., straighten or bend toward the longitudinal axis of the pull wire 560) from the first position to a second position, shown in FIG. 8C, to disengage from the barb 21a of the drainage stent 20. Once the engagement member 550 is disengaged from the barb 21a, the push catheter 14 may be withdrawn from the patient, leaving the drainage stent 20 at the desired location in the lumen.

In some instances, the first position may be an equilibrium position of the engagement member 550 (e.g., hook, tab). In other words, the engagement member 550 may be biased toward the first position, thus when an applied force is removed from the engagement member 550, the engagement member 550 may automatically revert back to the equilibrium first position. The engagement member 550 may be deflected toward the second position by applying a force to the engagement member 550, such as the force applied to the engagement member 550 by the barb 21a, as the pull wire 560 is withdrawn proximally. When not subjected to an applied force, the engagement member 550 may move back toward the first position.

Figure 9A:
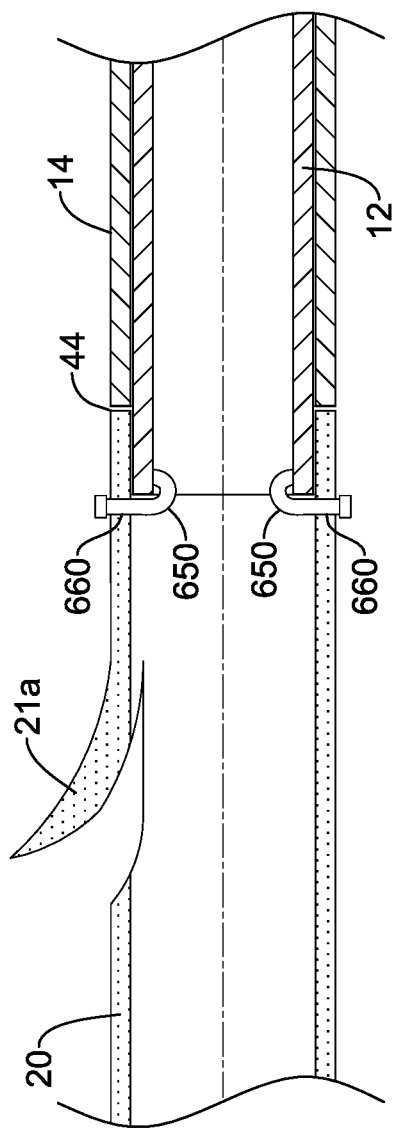
FIGS. 9A and 9B illustrate the functionality of yet another locking structure for selectively coupling a stent to an elongate shaft of a delivery system.
Figure 9B:
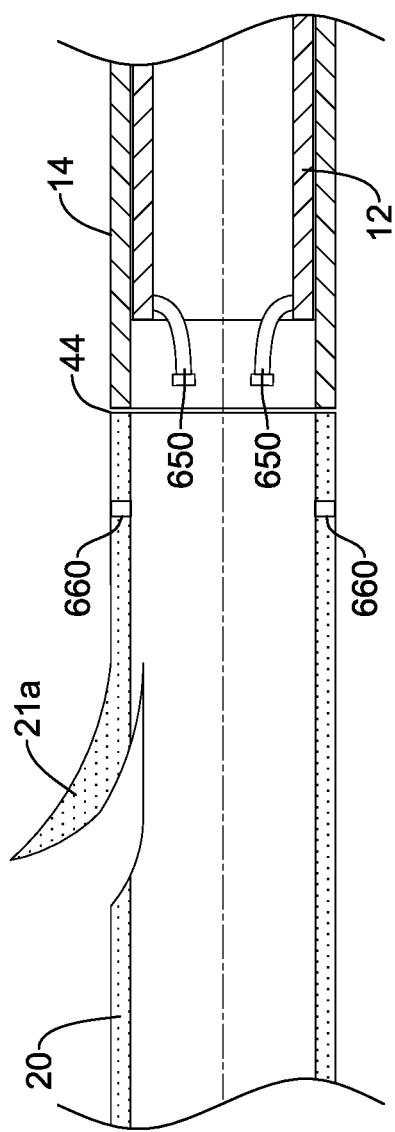

FIGS. 9A and 9B illustrate another exemplary embodiment of the distal end region of the guide catheter 12, including a coupling member configured for engagement with the drainage stent 20 to selectively couple the drainage stent 20 to the guide catheter 12. Although the drainage stent 20 is illustrated as being selectively coupled to the guide catheter 12 of the drainage stent delivery system 10, it is understood that in some embodiments the push catheter 14 may be so configured such that the drainage stent 20 may be selectively coupled to the push catheter 14, or another elongate shaft, in the manner described with regard to FIGS. 9A and 9B.

The guide catheter 12 may include one or more or a plurality of extensions 650 (e.g., fingers or whiskers) extending from the guide catheter 12. The extensions 650 may be attached and/or extend from the tubular wall of the guide catheter 12. In some instances, the extensions 650 may be formed of a compliant and/or elastomeric material such that the extensions 650 may be elongatable, stretchable, distensible, and/or deflectable when a force is applied to the extensions 650.

The extensions 650 may be configured to engage with an opening 660 or other engagement feature of the drainage stent 20 in order to interlock with and/or frictionally engage a portion of the drainage stent 20. For example, the extensions 650 may form an interference fit with a hole formed in the drainage stent 20, or the extensions 650 may be formed of a compliant material such that when the extensions 650, which may be sized slightly larger than the opening 660, are inserted into the openings 660 in the drainage stent 20 the extensions 650 fill the openings 660 and/or are compressed in the openings 660, forming an interference fit. In some instances, the extensions 650 may be notched or barbed to interlock with an edge of the openings 660 of the drainage stent 20.

FIGS. 9A and 9B show the drainage stent 20 selectively coupled to and decoupled from the guide catheter 12, respectively, by means of the extensions 650. As shown in FIG. 9A, the drainage stent 20 may be positioned proximate the distal end 30 of the push catheter 14 with the extensions 650 extending through the openings 660 of the drainage stent 20. With the drainage stent 20 coupled to the guide catheter 12, the proximal end 44 of the drainage stent 20 may face or abut the distal end 30 of the push catheter 14. In other embodiments, however, the proximal end 44 of the drainage stent 20 may overlap with the distal end 30 of the push catheter 14.

The drainage stent 20 may be decoupled from the guide catheter 12 by withdrawing the guide catheter 12 proximally from the lumen 48 of the drainage stent 20, as shown in FIG. 9B while the push catheter 14, abutting the proximal end 44 of the drainage stent 20, prevents the drainage stent 20 from moving. As the guide catheter 12 is withdrawn proximally relative to the drainage stent 20, extensions 650 may be elongated, stretched, distended, and/or deflected to release the extensions 650 from the openings 660. For instance, the guide catheter 12 may be withdrawn proximally such that the extensions 650 are stretched sufficiently, and thus decreased in cross-section sufficiently, to be removed from the openings 660. Once the drainage stent 20 is decoupled from the guide catheter 12, the push catheter 14 and/or the guide catheter 12 may be withdrawn from the patient, leaving the drainage stent 20 at the desired location in the lumen.

It is noted that any of the tabs or other engagement features described herein may be enhanced by coatings, surface treatments (e.g., ribs, grooves, knurling, teeth, corrugations etc.), tackiness, or other modifications which may enhance the frictional engagement and/or interlocking engagement between the drainage stent 20 and the guide catheter 12 and/or push catheter 14.

Although the disclosed engagement features (e.g., tabs) have been described as being included with a select component (e.g., drainage stent 20, guide catheter 12, and/or push catheter 14), it is noted that the engagement features (e.g., tabs) may be alternatively arranged on another component of the drainage stent delivery system 10 in a similar fashion, if desired, to selectively couple the drainage stent 20 to an elongate shaft of the drainage stent delivery system 10.

Although several illustrated embodiments of the disclosed stent locking structures are illustrated as being incorporated into a delivery system for delivering a drainage stent, it is understood that the stent locking structures may also be used to selectively lock other stent or endoprosthesis devices to a delivery system. For example, in some instances the stent locking structures described herein may be used to selectively lock a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system comprising:
   a drainage stent having a proximal end, a distal end, and lumen extending therethrough, the drainage stent including a flap along a length of a tubular wall of the drainage stent; and
   a pull wire extending distally from a handle assembly, the pull wire having an engagement member at a distal end of the pull wire extending to the drainage stent;
   wherein the engagement member is configured to selectively couple to the drainage stent between the flap and the tubular wall, wherein the engagement member extends transversely across the flap.

2. The stent delivery system of claim 1, wherein the flap comprises base connected to the tubular wall and a distal free tip extending from the base.

3. The stent delivery system of claim 2, wherein the engagement member is coupled to the drainage stent between the base and the distal free tip.

4. The stent delivery system of claim 1, wherein the engagement member is coupled to the drainage stent radially inward of the flap.

5. The stent delivery system of claim 1, wherein the engagement member has a hook, tab, or non-longitudinally bent shape.

6. The stent delivery system of claim 1, wherein an outer surface of the flap is continuous with an outer surface of the tubular wall.

7. The stent delivery system of claim 1, further comprising a push catheter over a proximal portion of the drainage stent and the flap.

8. The stent delivery system of claim 1, wherein flap extends radially outward away from the lumen from the tubular wall of the drainage stent.

9. A stent delivery system comprising:
   a drainage stent including a tubular member having a proximal end, a distal end, and lumen extending therethrough, the drainage stent including a flap extending radially outward from the lumen from an outer wall of the tubular member of the drainage stent; and
   a pull wire extending distally from a handle assembly and extending along the outer wall of the tubular member, the pull wire having an engagement member at a distal end of the pull wire positioned at least partially inside of the outer wall of the tubular member;
   wherein the engagement member is positioned at least partially inside of the outer wall in a first position to selectively couple the drainage stent to the pull wire, wherein the engagement member is movable from the first position to a second position, wherein the engagement member extends across the flap in the first position.

10. The stent delivery system of claim 9, wherein the engagement member is proximal to the flap in the second position.

11. The stent delivery system of claim 9, wherein the flap comprises base connected to the tubular wall and a distal free tip extending from the base.

12. The stent delivery system of claim 11, wherein the engagement member is coupled to the drainage stent between the base and the distal free tip in the first position.

13. A stent delivery system comprising:
   a push catheter having a proximal end, a distal end, and a lumen extending therethrough;
   a drainage stent extending from a distal portion of the push catheter, the drainage stent including a flap along a length of a tubular wall of the drainage stent; and
   a pull wire extending distally from a handle assembly, the pull wire having a distal engagement portion configured to selectively couple to the drainage stent between the flap and tubular wall, wherein the distal engagement portion extends transversely across the flap.

14. The stent delivery system of claim 13, wherein the distal engagement portion of the pull wire is movable between a first position and a second position.

15. The stent delivery system of claim 14, wherein the distal engagement portion engages the flap in the first position and the distal engagement portion disengages the flap in the second position.

16. The stent delivery system of claim 13, wherein the flap comprises base connected to the tubular wall and a distal free tip extending from the base.

17. The stent delivery system of claim 13, wherein the pull wire extends between the tubular wall and the push catheter.

* * * * *